United States Patent
Yu et al.

(10) Patent No.: US 6,905,875 B2
(45) Date of Patent: Jun. 14, 2005

(54) NON-DISRUPTIVE THREE-DIMENSIONAL CULTURE AND HARVEST SYSTEM FOR ANCHORAGE-DEPENDENT CELLS

(75) Inventors: Hanry Yu, Irvine, CA (US); Kam W. Leong, Ellicott City, MD (US); Ser-Mien Chia, Singapore (SG)

(73) Assignees: National University of Singapore, Singapore (SG); Agency for Science, Technology and Research, Centros (SG)

( * ) Notice: Subject to any disclaimer, the term of this patent is extended or adjusted under 35 U.S.C. 154(b) by 45 days.

(21) Appl. No.: 10/398,957

(22) PCT Filed: Oct. 12, 2001

(86) PCT No.: PCT/US01/31890

§ 371 (c)(1),
(2), (4) Date: Aug. 22, 2003

(87) PCT Pub. No.: WO02/31135

PCT Pub. Date: Apr. 18, 2002

(65) Prior Publication Data

US 2004/0023370 A1 Feb. 5, 2004

Related U.S. Application Data

(60) Provisional application No. 60/239,259, filed on Oct. 12, 2000.

(51) Int. Cl.$^7$ .......................... C12N 11/00; C12N 11/02; C12N 11/10
(52) U.S. Cl. .......................... 435/395; 435/182; 435/1.1; 435/123; 435/180; 435/320.1; 435/325; 435/366; 435/69.1; 435/69.7; 435/174; 536/23.1; 536/23.2; 514/963; 514/970; 264/4.32
(58) Field of Search ................................. 435/395, 182, 435/1.1, 123, 180, 320.1, 325, 366, 69.1, 69.7, 174; 536/23.1, 23.2; 514/963, 970; 264/4.32

(56) References Cited

U.S. PATENT DOCUMENTS

| 4,994,388 A | | 2/1991 | Hillegas et al. | |
|---|---|---|---|---|
| 5,620,883 A | * | 4/1997 | Shao et al. | 435/174 |

FOREIGN PATENT DOCUMENTS

| EP | 0 222 718 | 5/1987 |
|---|---|---|
| EP | 0 529 751 | 3/1993 |
| WO | WO 91/07485 | 5/1991 |

* cited by examiner

*Primary Examiner*—James O. Wilson
*Assistant Examiner*—Devesh Khare
(74) *Attorney, Agent, or Firm*—Banner & Witcoff, Ltd.

(57) ABSTRACT

A non-disruptive three-dimensional culture system allows cell growth and proliferation in three dimensions, permitting cell splitting without subjecting cells to disruptive conditions that affect cell structure and functions. An extracellular matrix provides a good environment for culturing or co-culturing anchorage-dependent cells. The cells cultured this manner can be readily used in such applications as cell transplantation, tissue engineering seeding of cells on scaffolds, and other applications that require immediate availability of functioning cells.

16 Claims, 10 Drawing Sheets

NON-DISRUPTIVE THREE-DIMENSIONAL CULTURE AND HARVEST SYSTEM FOR ANCHORAGE-DEPENDENT CELLS

CROSS-REFERENCE TO RELATED APPLICATION

This application is a National Stage application of co-pending PCT application PCT/US01/31890 filed Oct. 12, 2001, which was published in English under PCT Article 21(2) on Apr. 18, 2002, which claims the benefit of U.S. provisional application Ser. No. 60/239,259 filed Oct. 12, 2000. These applications are incorporated herein by reference in there entireties.

BACKGROUND OF THE INVENTION

1. Field of the Invention

This present invention is directed to cell culture and, more particularly, to a three-dimensional culture and harvest system for anchorage-dependent cells.

2. Description of Related Art

There has recently been a resurgence of interest in stem cell research. Stem cells are multi-potent and plastic, which enables them to be induced to differentiate into various cell types. Almeida-Porada et al., "Adult Stem Cell Plasticity and Methods of Detection," *Rev Clin Exp Hematol* 5(1), 26–41 (2001). Adult stem (AS) cells are preferable in most applications not only because the cell sources are less controversial and more readily available than embryonic stem (ES) cells, but also the adult stem cells are more easily induced into the final differentiated cell types needed in applications. Clarke, D. et al, "Differentiation Potential of Adult Stem Cells," *Curr Opin Genet Dev* 11(5), 575–580 (2001). To date, AS cells are not considered suitable substitutes for ES cells because of the differences in their proliferation capacity in vitro. Gage, F. H., "Mammalian Neural Stem Cells," *Science* 287 (5457), 1433–1438 (2000); NIH bioethics guideline. ES cells (especially in murine models) have essentially unlimited proliferation capacity in vitro, which means that they can be expanded greatly for applications. On the other hand, most AS cells can only proliferate for about 5–12 passages in vitro and then stop proliferating, but randomly differentiate into other cell types. Pittenger, M. F. et al., "Multilineage Potential of Adult Human Mesenchymal Stem Cells,"*Science* 284 (5411), 143–147 (1999). This characteristic has heretofore severely limited the usefulness of AS cells in therapeutic applications.

Most mammalian cells are anchorage-dependent (except cells in fluid, such as lymphatic and hematopoietic cells). In vitro culture of the anchorage-dependent cells traditionally has been limed by two primary factors. One is the limited space of the culture vessels. Cells will only proliferate exponentially in log phase when there is adequate room in the culture vessels. Once the cells establish contact with each other, their proliferation slows down and eventually stops or the cells even signal each other to die by apoptosis. The other limiting factor is the suitability of substrates for cell attachment. Inappropriate attachment often alters the cellular functions and all the observed structures and functions thereafter. Both factors cause potential artifacts that can affect the outcome of cell biological studies or cell-transplantation or tissue engineering applications.

Several approaches have been used to avoid contact inhibition of cell proliferation by providing sufficient space or surface on which the cells can grow. One approach has been to split cells by protease treatment to detach the cells from the culture surface before the cell-density becomes confluent. Trypsin is commonly used but others, such as collagenase, are also used in some circumstances. Protease-related cells typically are rounded up, collected, pelleted by centrifugation, re-suspended in fresh culture media, and distributed in multiple culture vessels. Each new vessel contains a fraction of the original cell number, and thus has sufficient new surface to allow cell proliferation until confluence again occurs. Such a splitting process can be repeated several times, until the cells stop proliferating due to other reasons.

Another approach has been to increase the time before successive cell splitting by lowering the minimum number of cells to be seeded into vessels or increasing the maximum number of cells that the culture vessel can accommodate before confluence. Because cells naturally prefer to be in the vicinity of other cells to support each other, the minimum number that can be seeded initially in culture vessel is often limited by the support rendered by cell—cell interaction, communication and the release of growth factors and the like. Therefore, enriched culture media have been used to support cell growth and proliferation, allowing lower minimum cell number to be seeded in the vessel, and allowing a longer period before the cells have to be split again.

Another way of increasing the time of culture between each split has been to grow cells in three-dimensional matrix. A three-dimensional matrix typically has a thick layer of matrix such as collagen on the surface of culture vessel, or microspheres of concentrated matrix. In such a three-dimensional matrix, cells can grow into multiple layers in 3 dimensions, thereby permitting a longer culture period before confluence. To modulate cell attachment to a substrate, various natural and synthetic substrates have been developed such as those involving short-peptides and sugar-motifs and the like.

Essentially all these approaches involve splitting cells with disruptive techniques such as proteases, cold treatment, or EDTA treatment combined with cell scraping to detach the cells from the substrate (either charged surfaces or three-dimensional matrix). Either of these splitting techniques can have detrimental effects on cell structure and function. For example, proteases digest away cell surface molecules that are essential not only for cell attachment to substrates but also for signaling molecules that are important for cell function. Cold treatment has been shown to adversely affect various cellular processes such as cytoskeleton arrangement, membrane trafficking pathways, and the like. EDTA treatment and mechanical scraping has been shown to adversely affect cell functions because the cells round up and are prone to damage by mechanical scraping. In the case of three-dimensional culture in matrix, protease treatment is the only way presently known to split cells. For cell transplantation or cell seeding onto tissue-engineered scaffolds, cells with temporarily damaged functions (due to disruptive cell splitting techniques) are currently being used because the current culture methods cannot offer a better alternative.

SUMMARY OF THE INVENTION

The present invention is directed to a non-disruptive three-dimensional system for culturing one or more anchorage dependent cell types. The culture system comprises a plurality of microcapsules having an inner extracellular matrix surrounding at least one cell and an outer shell of synthetic polymer surrounding the extracellular matrix. The microcapsules are permeable to nutrients necessary to sustain normal metabolic functions of the cells and to toxins released by the cells. The outer shell has a thickness of from about 1 to about 40 $\mu$m.

The three-dimensional culture system allows cell growth and proliferation in three dimensions, allowing cell splitting without subjecting cells to disruptive conditions that affect cell structure and functions. The matrix used in the system also provides a good environment for culturing or culturing anchorage-dependent cells. The cells cultured this me can be readily used in cell transplantation, tissue engineering seeding of cells on scaffolds, and other applications that require immediate availability of functioning cells. The culture system of the present invention employs mechanically fragile microcapsules that easily break during the cell splitting process. The positively charged collagen preferably is optimized to be sufficiently diluted inside microcapsules, such that the collagen can be easily rinsed away from cells during cell splitting.

The non disruptive three-dimensional cell culture system allows anchorage dependent cells to be cultured in the microcapsules and to be harvested without the need of subjecting the cells to harsh treatment such as proteases, cold or cell scraping. The harvested cells cultured this way are readily used for cell transplantation or cell seeding onto scaffold for tissue engineering applications. Cells cultured with current systems, in contrast, are somewhat damaged by the harvest procedure.

The three-dimensionality of the system is designed to amplify large number of cells with reduced cell splitting frequency. The system also allows harvest of cells for re-proliferation or for immediate use in applications without undergoing the typical detachment procedures. The cells harvested non-disruptively from the cell culture system of the present invention typically exhibit improved attachment kinetics, better-preserved cell morphology and functions than conventionally cultured cells when binding to ligand-conjugated polymer surfaces.

The cell culture system of the present invention is useful in cell-based analyses or diagnostic methods, such as flow cytometry analyses, that depend on the cell surface markers. Currently, such analyses are only applicable to suspension cells such as hemopoietic cells. Examples include using Annexin V as marker for apoptosis, $Ca^{++}$ kinetics or cytoskeleton markers that are sensitive to cell harvesting conditions such as protease, cold or EDTA treatments. The present invention enables these analyses to be applied to all other cell types that are anchorage-dependent.

Three-dimensional culture is more like the natural setting of cells, which is demonstrated by higher level of cell functions than those from two-dimensional culture. There is also more room for cells to proliferate, thereby increasing culture time before cell splitting is necessary. This also results in smaller number of seeded cells and larger number of harvested cells. Such characteristics are ideal for large-scale cell production. Previous three-dimensional methods are hampered by the difficult cell splitting and harvesting procedures. The present invention overcomes the drawbacks of previous three-dimensional methods.

Because the use of enzyme, chemicals or temperature change is not needed in the three-dimensional cell culture system during cell splitting, the process of the cell splitting is greatly simplified and the cost and storage of enzymes used to split cells can be minimized. This is particularly advantageous for large-scale production and passage of anchorage-dependent cells.

Each microcapsule serves as an independent microchamber for cell culture thus allowing the microcapsules to be used in any bioreactor design. The mass transport property of the microcapsules is good enough to allow cell culture in even stationary culture vessels. This can be achieved, for example, with a low concentration of the extracellular matrix. Where collagen is used as an extracellular matrix, for example, the concentration typically ranges from about 0.2 to about 3.5 mg/ml. In previous systems using collagen as matrix, higher concentrations of collagen (4–5 mg/ml) were used because it was necessary to have the collagen gel and form the shape of the spherical droplet, and then coated with poly-L-lysine. Higher concentrations of the extracellular matrix tend to have skin effect that impedes the mass transport properties. Therefore, the previous microcapsules must be used in fluidized bed bioreactor to achieve improved mass transport for sufficient nutrient and gas supply for cell culture. The microcapsules of the present invention can be used with any bioreactor design. Especially in the case of packed bed, the culture media volume used can be kept at minimum.

BRIEF DESCRIPTION OF THE DRAWINGS

The present invention will now be described in more detail with reference to preferred embodiments of the invention, given only by way of example, and illustrated in the accompanying drawings in which:

FIG. 2A is a graph illustrating collagen gelation measured at 37° C. by the increase in refractive index; FIG. 2B is a confocal image showing collagen labeled with FTTC;

FIG. 5A is a graph illustrating attachment of PC 12 cells onto YIGSR conjugated to polyester cover slip; FIG. 5B is a graph illustrating attachment of rat hepatocytes on lactose-conjugated polyester membrane; FIG. 5C illustrates the morphology and function of the PC 12 cells; FIG. 5D is a graph illustrating the detoxification function of the rat hepatocytes; FIG. 5E are images showing morphology and proliferation capacity assessment of the MSc cells after a month of continuous culture; and FIG. 5F illustrates the doubling time of undisrupted cells and of conventionally cultured cells.

DETAILED DESCRIPTION OF THE INVENTION

Figure 1:
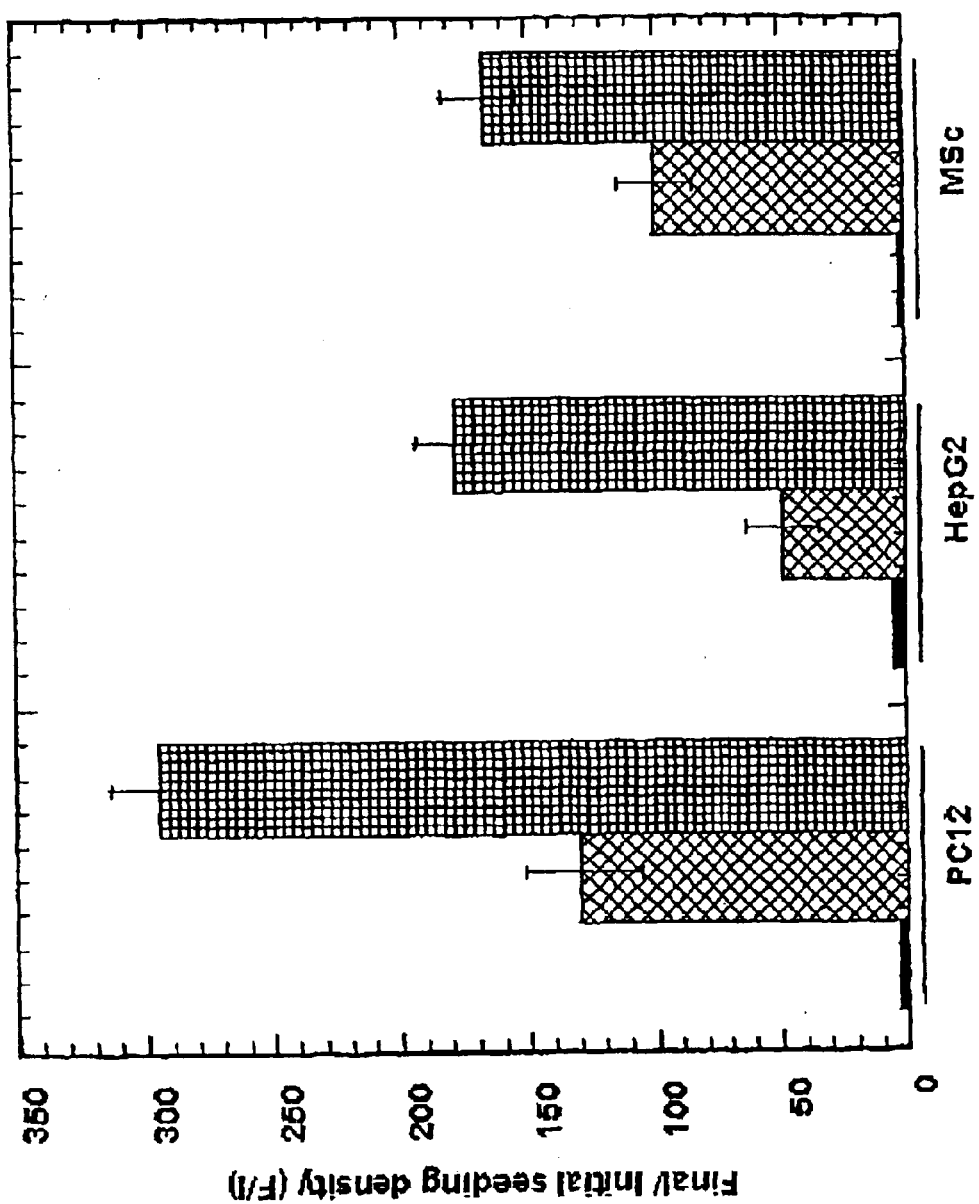
FIG. 1 is a graph illustrating PC 12, HepG2, and mesenchymal stem (MSc) cells being greatly amplified in the microcapsules without splitting.

The three-dimensional cell culture system of the present invention employs fragile microcapsules with a controlled three-dimensional microenvironment for optimal cell growth, proliferation and function. Microcapsules in the form of spheres have the highest surface area-to-volume ratio, and preferably have an ultra-thin shell allowing good mass-transport properties, thereby avoiding central necrosis resulted from nutrient/oxygen starvation as typically is observed in present three dimensional culture configurations. In a preferred configuration of the present invention, essentially the only role of the outer shell is to provide a container to hold the extra-cellular matrix inside the spherical shape to provide a substrate for the cells. To this end, a minimal concentration of the matrix sufficient to support cell growth, proliferation and function can be employed. For example, when collagen is used as an extracellular matrix, the concentration typically ranges from about 0.2 to about 3.5 mg/ml, and more typically from about 0.5 to about 1.5 mg/ml, in contrast to the 4 to 5 mg/ml typically used to entrap cells in present three-dimensional culture configurations.

Among the principal advantages associated with the three-dimensional cell culture system of the present invention are those exhibited in cell splitting and cell harvesting. Advantageously, the matrix does not need to gel to hold the cells in place. Therefore, when the fragile shells are broken at the time of cell splitting, the dilute matrix can be easily removed from cells by pelleting the cells and rinsing them with fresh culture media or buffers. The cells can be split int small fractions, diluted with new matrix and be microencapsulated and cultured again. The process can be repeated without subjecting cells to any harsh conditions that are disruptive to cell structures and functions. The cells are healthier than those cultured in conventional systems due to a more natural and constant culture environment without the need for subjecting the cells to periodic harsh treatments. Oxygen concentration often is the limiting factor in such three-dimensional cell culture. The microcapsule preferably should be less than about 200 $\mu$m in diameter.

The fragility of the microcapsules is an important aspect of the non-disruptive dimensional culture system. Weak mechanical force, such as pipetting up and down a few times, generally is sufficient to break the microcapsules and release the microcapsule contents, e.g., the matrix and the cells. Cells then can be separated from the dilute matrix by rinsing with buffers or culture media. The fragility of the microcapsules can be accomplished by employing a very thin microcapsule shell. The microcapsule shell usually has a thickness up to about 40 $\mu$m, often from about 1 to about 20 $\mu$m, and even more often from about 2 to about 5 $\mu$m A wide variety of anchorage-dependent cells can be used with the three-dimensional cell culture system of the present invention. PC-12, a rat pheochromocytoma cell that is normally cultured on collagen and which has the ability to be induced into neuron-like cells, is one example of an anchorage-dependent proliferating cell. As another example, hepatocytes are very environmentally sensitive anchorage-dependent cell. HepG2 is an example of a human hepatocellular carcinoma cell. Mesenchymal stem (MSc) cells are multipotent cells that can replicate as undifferentiated cells and that have the potential to differentiate to lineages of mesenchymal tissues. Other cells that have very strong cell—cell and cell-matrix interaction, such as keratinocytes, also are useful with the culture system of the present invention. The three-dimensional system of the present invention is particularly useful for the expansion of co-cultures, e.g., by including one than one cell type in the microcapsules.

The three-dimensional cell culture system of the present invention is useful in a variety of tissue engineering and cell transplantation applications, such as enzyme-free culture and exon of keratinocytes for skin, or chondrocyte or mesenchymal stem cells for cartilage/bone. In addition, the culture system is useful in applications that require or prefer three-dimensional culture of anchorage-dependent cells for either research purposes or for the production of eukaryotic cells or cell-secreted products. The culture system can be used in ex vivo cell production and genetic modifications of cells for transplantation theories to treat cancer, infectious diseases and tissue restoration. The culture system also is useful in cell-based diagnostic or analysis that depends on the natural states of cells (either from normal or pathological samples) without subjecting the cells to harsh protease treatments.

Cells can be cultured in the microcapsules with the matrix inside, while mass transport properties are optimized to avoid central necrosis. Typically, about $1 \times 10^5$ cells are seeded inside the microcapsules. The cells typically are allowed to proliferate for a period of days, usually 7 to 9. At the end of a culture cycle, the ratio of the final cell number to the initial seeded cell number typically is at least 10, and more typically at least 20. The ratio can be as higher as 100, 200, 400, 600, or more. This ratio demonstrates a much longer time (8–9 days) of cell culture between each successive cell splitting as compared to conventional two-dimensional culture (2 days assuming the same cell doubling time of 24 hours). The culture media should be changed every 2–3 days to provide fresh supply of nutrients and to remove metabolic waste. Depending on the mechanical strength of the microcapsules, the cells can be culture in stationary vessels or in packed bed for reduced consumption of culture media in large-scale cell culture. In the latter case, simple apparatus and minimum culture media can be employed for large-scale production of anchorage-dependent cells.

Both naturally-occurring and modified biopolymers are suitable for use as the extracellular matrix in the practice of the invention, as are both cationic and anionic biopolymers. In genera, any commonly used substrates in cell studies can be used, non-limiting examples of which include collagen, cationic collagen, anionic collagen, anionic esterified hyaluronic acid, anionic amine-modified hyaluronic acid, fibronectin, and laminin. The biopolymers preferably are water-soluble and most often have a molecular weight of at least 20,000, preferably at least 75,000, more preferably at least 125,000, even more preferably at least 200,000, and yet even more preferably at least 250,000.

Whereas collagen has been used to encapsulate drugs, it has not found widespread use for encapsulating cells because, at neural pH, there is insufficient charge density to form an encapsulating membrane. However, collagen modified to raise its pKi to at least about 9 is sufficiently positively charged at physiological pH to be complexed with oppositely-charged synthetic polyelectrolytes to form a coherent membrane. Collagen can be modified to form a more strongly basic polymer by converting the primary amino groups to tertiary amine groups or by esterification.

Anionic biopolymeric materials, such as hyaluronic acid (HA) and modified HA (esterified HA or amine-modified HA) are useful in the invention. In general, anionic biopolymers suitable for the practice of this invention will have a charge density of at least about 20%, preferably at least about 30%, and even more preferably at least about 50%. HA that is totally or partially esterified or reacted with a primary amine to render it less water-soluble will form a stronger complex with the polycationic outer layer than HA itself. Preferred biopolymers for forming the extracellular matrix include modified HA and modified collagen. Esterified collagen is particularly preferred. In general, the extracellular matrix, though water-soluble, will be slightly hydrophobic.

Esterification or reaction to form tertiary amine groups on the biopolymer may be accomplished by reaction of the biopolymer with a wide variety of aliphatic reactants containing as many as about 18 carbon atoms in their chain. Such reactants include, inter alia, alcohols, primary amines and alcohol amines. Preferred reactants contain about 8 carbon atoms or less. For some purposes, use of reactants having only 2 or 3 carbon atoms may be preferred. Typical alcohols include methanol, ethanol, butanol and higher alcohols, whereas typical primary amines include methylamine, ethylamine and higher amines. Reactants with both alcohol and amine groups also can be used, such as ethanolamine. Reactants should be chosen so as to not impair the viability of the cells.

The outer shell comprises a biocompatible synthetic polyelectrolyte having a charge opposite that of the biopolymer. Thus, when the biopolymer is polycationic (e.g., modified collagen), the synthetic polyelectrolyte used in the outer layer should be polyanionic. Conversely, when tee biopolymer is polyanionic (e.g., HA, modified HA, etc.), the synthetic polyelectrolyte used in the outer shell should be polycationic. Suitable outer layer synthetic polyelectrolytes form a complex with the oppositely-charged biopolymer to form a membrane by the complex coacervation process and impart stability to the encapsulate. The charge density of the synthetic polymer typically will be from about 0.1% to about 20%, preferably is at least about 1%, and even more preferably is at least about 3%. Like the biopolymers, the synthetic polyelectrolytes preferably have a molecular weight of at least 20,000, preferably at least 75,000, more preferably at least 125,000, even more preferably at least 200,000, and yet even more preferably at least 250,000.

The biocompatible synthetic polyelectrolyte layer that is capable of forming, with the biopolymer of the extracellular matrix, a membrane which allows environmentally-sensitive living cells, such as hepatocyte cells, to remain viable and, at the same time, protects the cells against immunological rejection by the host A preferred class of biocompatible synthetic polyelectrolytes is acrylate polymers. Such polymers include acrylate polymers, copolymers and ter-polymers such as poly(acrylic acid), poly(methacrylic acid), poly(methacrylate), poly(methyl methacrylate), and acrylate copolymers and ter-polymers of acrylic acid, methacrylic acid, methacrylates, methyl methacrylates, hydroxyethyl methacrylic such as 2-hydroxyethyl methacrylate, hydroxypropyl-acrylate and the like, and blends thereof. Poly(dimethylaminoethyl methacrylate) (DMAEMA) and copolymers and terpolymers of dimethylaminoethyl metacrylate with 2-hydroxyethyl methacrylate and/or hydroxypropylacrylate and methacrylate and/or methyl methacrylate are preferred cationic synthetic polymers. Copolymers or ter-polymers of acrylic acid and/or methacrylic acid with 2-hydroxyethyl methacrylic and/or hydroxypropylacrylate and methacrylate and/or methyl methacrylate are preferred anionic synthetic polymer. Each has exhibited biocompatibility when used in other biomaterials.

A preferred biocompatible synthetic polyelectrolyte outer shell is an acrylate ter-polymer of methacrylic acid (MAA), hydroxyethyl methacrylate (HEMA), and methyl methacrylate (MMA). The ter-polymer preferably comprises from about 10 mol % to about 30 mol %, more preferably from about 15 mol % to about 25 mol % MAA, from about 10 mol % to about 40 mol %, more preferably from about 20 mol % to about 30 mol % HEMA, and from about 20 mol % to about 60 mol %, more preferably from about 45 mol % to about 55 mol % MMA. In a preferred embodiment of the present invention, the ter-polymer is formed by polymerizing MAA, HEMA, and MMA monomers in about a 1:1:2 molar ratio.

The membrane of the encapsulated cell is selectively permeable. The cells encapsulated in accordance with the invention remain viable because the membrane is permeable to nutrients and other materials necessary to support the normal metabolic functions of the cells. Thus, ionic materials and oxygen, for example, pass through the membrane. The membrane also is permeable to products of the cells, such as hormones, and to metabolic byproducts. Thus, material produced by the cell can pass through the membrane from the interior of the microcapsule. In this way, material produced by the encapsulated cell can be introduced into the blood of a host, or can be introduced into a culture medium in which encapsulated cells are placed.

The membrane permeability essentially precludes entry of immunoglobulins, macrophages, and other immune system agents that cause rejection of cells by the host's ime system. According to a preferred embodiment of the invention, the membrane is impermeable to molecules greater than about 100 kDa, and preferably is impermeable to molecules greater than about 71 kDa. According to another preferred embodiment of the invention, the membrane is permeable to molecules greater than about 60 kDa and impermeable to molecules greater than about 150 kDa.

The composition of the outer shell can be modified to adjust the permeability and transport properties of the membrane. As an example, the permeability of the membrane to typically polar compounds found in biological systems can be increased by incorporating a hydrophilic copolymer, such as poly(2-hydroxyethyl methacrylate) (HEMA) or other hydroxy-containing acrylates, into the polyelectrolyte which forms the outer layer of the membrane. Increasing hydrophobicity of polyelectrolytes tends to cause decreased permeability.

In the preferred MAA/HEMA/MMA ter-polymer, HEMA provides hydrophilicity to render the ter-polymer water-soluble so that the entire encapsulation can be performed in the physiological aqueous buffer without the need for an organic solvent. MMA imparts mechanical strength, toughness, and elasticity to the microcapsules. MAA provides a negative charge to interact with a positively charged inner layer. The inner layer preferably is an esterified collagen with net positive charge. The balance between the two charged polymers determines the physical characteristics of the microcapsules. Using a 10% ter-polymer and 1.5 mg/ml of modified collagen, for example, microcapsules can be formed having a thin layer of outer shell (−2 pin) and a semi-ge-like inner layer that minimizes impedance to mass transport across the membrane but remain stable as microcapsules for days. The semi-gel-like inner collagen layer is able to provide a "loose" extracellular matrix configuration that mimics the in vivo situation, therefore allowing the microcapsule to maintain higher levels of cell function. These characteristics of the microcapsules that satisfy most requirements for a bioartificial liver-assisted device (BLAD) were achieved through optimization of several parameters.

The permeability of the membrane also can be adjusted by selection of molecular weight or structure of the outer shell so as to preclude molecules having a preselected molecular weight or structure from passing through the membrane. As the molecular weight of the polyelectrolyte is increase the membrane tends to be more permeable. Larger differences in charge densities between the inner biopolymer and the outer polyelectrolyte also tend to make the membrane more permeable. Th mechanical stability of the membrane can be improved by increasing the molecular weight of the polyelectrolyte in the outer shell or by employing monomers in the polyelectrolyte that provide mechanical strength, such as MMA.

The membrane can be formed by complex coacervation by combining drops of a solution of biopolymer containing a cell suspension with a solution of synthetic polymer at physiological or neutral pHs of from about 6 to about 8 so as to avoid adversely affecting the viability of the cells. In such process, the biopolymer is dissolved in a suitable aqueous solvent that will not adversely affect the viable cells. Such solvents are well known and include buffered saline, culture medium and the like. Similarly, the synthetic polyelectrolyte is soluble in and dissolved in a suitable solvent that will not threaten the viability of the cells. Such solvents include aqueous solvents such as buffered saline, culture medium and the like. The solvent used for the biopolymer does not need to be the same solvent used for the synthetic polymer. Mild agitation of the polyelectrolyte solution can be utilized if desired.

In one suitable technique, a substrate polymer solution containing a cell suspension in a suitable diluent such as phosphate buffered saline (PBS) is added dropwise to a receiving solution containing synthetic polyelectrolyte of the opposite charge in PBS at ambient temperature. A cohesive membrane is formed at the interface of the two solutions to provide encapsulated cells. Advantageously, no organic solvent is required and no cross-linking reaction is necessary. Thus, the conditions of encapsulation are especially mild, yielding little cell mortality.

The proper matching of biopolymer and synthetic polyelectrolyte can be readily confined. A drop of a solution of biopolymer can be added to a solution of electrolyte. A proper match results in the rapid formation of a microcapsule or membrane by complex coacervation, which can be observed visually. The suitability of a given encapsulate regarding permeability can be readily determined by in vitro tests using standard cell culture media to determine if desired products are secreted, if unwanted immune components are excluded, and if viability of encapsulated cells is suitably maintained.

The concentrations of the polymer solutions, the size of the droplets added to the synthetic polyelectrolyte solution, and the rate at which the substrate polymer solution containing cell suspension is added to the synthetic polyelectrolyte solution can be adjusted to achieve an encapsulating membrane having the desired thickness of layers and desired size. Suitable concentrations for the biopolymer solution and for the synthetic polyelectrolyte solution will vary depending upon the specific polymers and solvents employed, but determination of such concentrations is easily within the skill of the art. While it is not possible to delineate concentrations for all possibilities, the concentration of the biopolymer often will be from about 0.1 to 2% whereas the concentration of the synthetic polyelectrolyte often will be from about 2 to 6%.

The thickness of the inner, substrate polymer layer, will depend on, inter alia, the viscosity of the biopolymer solution and the degree of penetration into the synthetic polyelectrolyte solution achieved by the substrate polymer solution droplets. The degree of penetration is related to the molecular weight of the polyions and the viscosity of the solutions.

The number of cells within each microcapsule can be readily controlled and is a function of the density of the cell suspension within the biopolymer. For example, cells in PBS (which may be at densities of 10 to 10 cells per ml) can be mixed with the biopolymer to provide a variety of cell concentrations. Individual microcapsules can contain any desired number of cells, typically ranging from 1 to 200 cells or more. Collagen gel has been observed to exhibit a "skin effect" that is detrimental to mass transport, as a high concentration of collagen leads to gelation. Such "skin effect" is concentration- and temperature-dependent. Extracellular matrices like collagen or Matrigel have gelling temperatures of 22–35° C. depending on the concentration of these proteins. At 37° C., where hepatocytes are normally cultured in a bioreactor or transplantation is performed in vivo, the "skin effect" can be most pronounced. Since mass transport is among the most important considerations for the design of bioreactors in BLAD, it is desirable to employ the optimal concentration of collagen such that the "skin effect" is minimized while there still is enough collagen to complex with the synthetic polyanion forming stable microcapsules.

Albumin was used as a model molecule for the permeability optimization of the microcapsules. Albumin (MW 67,000 Da) is one of the secreted proteins of hepatocytes. It acts as a carrier to bind most metabolic wastes in the liver for removal from the blood. Another major scavenger protein is bilirubin (–10,000 Da), which is smaller than albumin. Albumin was found to be freely permeable to the microcapsules. A known concentration (1% w/v) of albumin was added to collagen and microcapsules were formed. The microcapsules were equilibrated in a culture medium with the same concentration of albumin (1% w/v) at 37° C. for 2 hours to allow a possible "skin effect" to occur. Such equilibration before the permeability measurements is essential for detecting any "skin effect" from the gelling collagen. Pre-equilibration for up to 5 days indicated that the "skin effect" was marginally more pronounced than with the 2 hour pre-equilibration. The albumin released from the microcapsules into the fresh culture medium with no albumin added was thereafter monitored. With 1.5 mg/ml of the modified collagen, most of the encapsulated albumin was released from the microcapsules within 15 minutes. As the concentration of collagen in the microcapsule was increased to 4 mg/ml (–0.4% w/v), the release of albumin was greatly inhibited. For collagen concentration below 1.5 mg/ml, hepatocytes could not be encapsulated, possibly due to insufficient positive charge from the diluted collagen.

One preferred ter-polymer composition is made up of 25 mol %/25 mol % MAA and 50 mol % MMA at a concentration of 10% in PBS. When the ter-polymer composition was modified for higher negative charge at the expense of mechanical stability (e.g., 50 mol % MAA, 25 mol % HEMA, 25 mol % MMA), the urea-synthesis of the encapsulated hepatocytes decreases to levels below the monolayer control. The polymer composition and concentrations can be varied to achieve enhanced mechanical stability and other physical characteristics.

Because the membrane of the encapsulated cells of the invention precludes contact between the cells and the hoses immune mediators, all types of living cells, including both naturally-occurring and genetically-engineered cells, may be encapsulate. The encapsulates are suitable for anchorage-independent cells and are particularly suitable for encapsulation of environmentally sensitive, anchorage-dependent living cells such as hepatocytes.

Encapsulated cells of the invention also are useful as, for example, a hormone-producing system. Use of cells microencapsulated in a selectively permeable bio-polymeric membrane affords the opportunity to provide artificial organs and other methods for improving and restoring functions in people with physical disabilities.

An example of one type of hormone-producing cell is a cell of the anterior pituitary gland. Such cell excretes growth hormone that inter alia stimulates skeletal growth. In accordance with the invention, encapsulated naturally occurring anterior pituitary cells are useful in stimulating skeletal growth in a host. The encapsulated cells provide growth hormone produced by the cells and introduced to the blood of a host though the encapsulating membrane. Genetically-engineered microorganisms also can produce growth hormone. Such microorganisms, when encapsulated, may be used to provide growth hormone to a host.

Encapsulated cells that sect hormones also may be suspended in a culture medium and will excrete hormone over an extended period. Encapsulated insulin-producing cells, for example, mammalian pancreatic alpha cells, beta cells, or intact islets of Langerhans, may also be used as an artificial pancreas. Such encapsulated cells can be implanted into a diabetic mammal and will function in vivo to excrete insulin and other hormones in response to host blood glucose concentration.

Other types of cells also may be beneficially encapsulated. For example, encapsulated neurotransmitter-secreting cells may be used to treat neurological disorders such as Parkinson's and Alzheimer's diseases. Similarly, chromaffin cell transplants may be used for alleviation of pain, especially chronic pain, and encapsulated chondrocytes may be used for repair of musculoskeletal defects. Skilled practitioners recognize the utility of encapsulating living cells, and will be able to identify still further cells suitable for encapsulation in accordance with the invention.

Even though the membrane may be permeable to proteases that can digest collagen and other biopolymers used to form the inner layer of the membrane, it has been found that the inner layer remains intact. Without being bound by any theory, it is believed that the proteases cannot digest the modified collagen, HA, modified HA, or other biopolymer when the biopolymer is complexed with the outer layer. This resistance can be analogized to the resistance to solubilization of type I collagen and to cross-inked collagen, such as is found in heart valve tissue. Again, without wishing to be bound by theory, it is postulated that the complexation shields or changes the conformation of the cleavage site (between glycine and leucine), thus making the resulting complexed biopolymer resistant to degradation.

The length of the period during which encapsulated cells remain intact will depend upon the properties of the medium in which the encapsulated cells are used and upon the composition of the biopolymer and of the synthetic polyelectrolyte. For example, encapsulated cells used in a culture medium might be expected to remain intact for a longer period than encapsulated cells introduced into a human or animal body. Also, the mechanical stability of the membrane can be improved by increasing the molecular weight of the synthetic polyelectrolyte. Skilled practitioners will be able to determine the length of the period during which encapsulated tells remain intact in various media.

The three-dimensional culture system of the present invention supports the proliferation of anchorage-dependent mammalian cell. Three exemplary anchorage-dependent mammalian cell types of interest are (1) PC 12, a rat pheochromocytoma cell that is normally cultured on collagen, (2) HepG2, a human hepatocellular carcinoma cell, and (3) mesenchymal stem (MSc) cells, which are multipotent cells that can replicate as undifferentiated cells and that have the potential to differentiate to lineages of mesenchymal tissues. As shown in FIG. 1, all of these cell types can proliferate in the microcapsules. The cells can proliferate, for example, when seeded at the density range of about $5 \times 10^4$ to $2 \times 10^6$ cells/ml with the optimal density at about $1 \times 10^6$ cells/ml which yielded over 100-fold cell amplification (defined as the final/initial cell densities in microcapsules) in 7 days.

In comparison, cells on the conventional two-dimensional surfaces coated with collagen (referred to for simplicity as "2D culture") could only proliferate when the cells were seeded within the narrower density range of $1 \times 10^5$ to $7 \times 10^5$ cells per 35 mm dish. Below a cell seeding density of about $1 \times 10^5$ cells/dish, the cells did not proliferate and often detached from the collagen surfaces within two days. Above about $7 \times 10^5$ cells/dish, the cells were essentially confluent in the 2D culture and did not proliferate due to contact inhibition. The three-dimensional microenvironment of the microcapsules is more permissive for anchorage-dependent cells to proliferate before encountering contact inhibition.

With a cell seeding density of about $1 \times 10^6$ cells/ml, the effects of different collagen concentrations on the proliferation of the PC 12 and HepG2 cells in the microcapsules were evaluated. It was found that cells could proliferate in the collagen concentration range of 0.5–5.0 mg/ml, with the optimal concentration at about 1.5 mg/ml. In the experiments described below, $1 \times 10^6$ cells/ml of the PC12, HepG2 and MSC cells were cultured in 1.5 mg/ml of collagen.

It was found that the three-dimensional culture system with positively charged collagen minimizes cell splitting. One of the ways to avoid disrupting cells too often in culture is to allow the cells to proliferate for as long as possible before splitting. Since the microcapsules can accommodate more anchorage-dependent cells than the 2D culture within the same culture volume, the microcapsules can potentially allow a longer period of cell culture to achieve greater cell amplification before cell splitting is needed. Indeed, PC 12, HepG2, and MSc cells can be cultured for 7 days in the microcapsules of the present invention before the cells filled the microcapsules and cell splitting became necessary. The longest permissive culture time before cell splitting and the level of cell amplification between each successive cell splitting depend on the proliferation rates of cells under the culture conditions employed. In 7 days, PC 12, HepG2, and MSc cells were amplified 130±7, 50±3, and 100±8 folds, respectively, in the microcapsules, as compared to the typical 2–10 folds of cell amplification and 2–3 weekly splitting in 2D culture, as shown in FIG. 1. The folds of amplification (defined as the ratio of the final cell density to the initial cell density) are shown in FIG. 1 (F/I). The symbol ■ represents the F/I values for cells cultured in 2D; the symbol ■ represents the F/I values for cells cultured in microcapsules with the slightly modified collagen; and the symbol ⊠ represents the F/I values for cells cultured in microcapsules with highly modified collagen. All three cells were amplified greatly in the microcapsules, but not in the 2D culture. The additional net positive charges on the highly modified collagen alone could double the amplification of cells cultured in microcapsules.

Because many cells are known to respond to electric signals in the microenvironments, it is believed that the net positive charges on the modified collagen contribute to the observed higher level of cell amplification in the microcapsules than the 2D culture. To demonstrate this, different amounts of net positive charges on the collagen were controlled by manipulating the temperature and the time of the collagen modification. Using a highly modified collagen (the preparation of which is described below), greatly stimulated cell amplification was observed. The PC 12, HepG2, and MSc cells were amplified 295±19, 170±9, and 163±12 folds, respectively, in the microcapsules with the highly modified collagen (FIG. 1). It is believed that the additional net positive charges alone on the collagen matrix could double the amplification of cells cultured in the microcapsules.

The cultured cells eventually must be split for re-proliferation or harvested for immediate applications. To minimize or avoid the cell damages caused by detachment procedures commonly used in cell splitting or harvesting, the culture system of the present invention preferably allows cells to be separated from each other but not from the supporting substrata. This is possible because of two unique properties of the culture system, namely, the positively charged modified collagen with reduced gelation (FIG. 2), and the fragile microcapsule shell (FIG. 3). The upper part of the image of FIG. 3 shows the intact portion of the microcapsule showing that a very thin and fragile layer of the shell wraps around the encapsulated cells. The lower part of the image of FIG. 3 shows the broken portion of the microcapsule showing that the encapsulated cells are supported by loose collagen fibers.

Figure 2A:
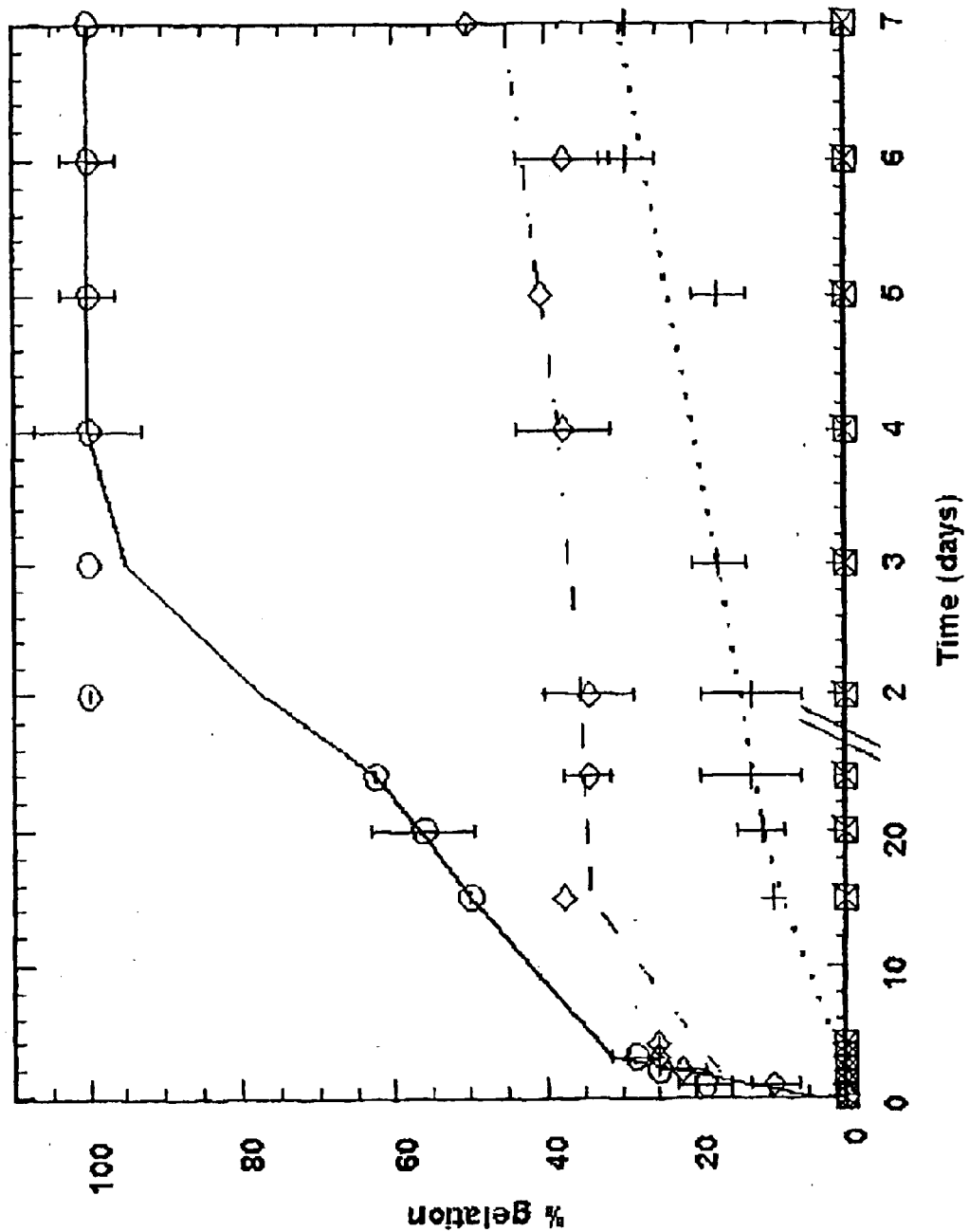
FIGS. 2A–2B illustrate "conformer scaffolds" formed around individual cells and allow cell splitting or harvesting without detachment from the substrata.
Figure 2B:
Figure 3:
FIG. 3 is a scanning electron microscope (SEM) image of a microcapsule in which a portion of a microcapsule was peeled off exposing the cells encapsulated inside.

As shown in FIG. 2A, the modified collagen with net positive charges has a reduced level of gelation than the natural collagen as measured in a refractive index assay. The symbol (○) represents the natural collagen (1.5 mg/ml); the symbol (□) represents slightly modified collagen (1.5 mg/ml); the symbol (x) represents highly modified collagen (1.5 mg/ml); the symbol (◇) represents slightly modified collagen (5 mg/ml); and the symbol (+) represents highly modified collagen (5 mg/ml). The positive charges on the modified collagen inhibit the collagen gelation. In such an assay, 1.5 mg/ml of the native collagen started exhibiting elevated refractive indices 1 hour upon incubation at 37° C. Therefore, the kinetics of the increase in refractive index coincided with the kinetics of the natural collagen gelation. The more positively charged the collagen, the less gelation was observed. Because cell surfaces are negatively charged due primary to the negative charges on the glycoproteins and the sialic acid of glycolipids, it is believed that the negatively charged cell surfaces can neutralize the positively charged modified collagen immediately surrounding the cells, and induce the neutralization of a thin layer of collagen to gel. In other words, a layer of collagen fibers is expected to form around the cells, soon after the cells were mixed with the positively charged collagen.

When the modified collagen was labeled with a fluorescence dye (Fluorescein isothiocyanate, FITC) and formed microcapsules with the labeled modified collagen, a layer of collagen fibers was observed around the cells (FIG. 2B) within 5 minutes. Such collagen fibers conforming to the shapes of the cells could support the proliferation and functions of the anchorage-dependent mammalian cells (such collagen fibers are referred to herein as the "conformer scaffolds").

Further away from the cells, the positively charged modified collagen remained in the liquid state, or had loose collagen fibers (FIG. 3) not inter-linked as in a dense gel. Therefore, the liquid collagen could be removed from the cells with a buffer rinse after passing the microcapsules through a nozzle of approximately 1 mm inner diameter at a flow rate of 8 ml/min to break the fragile microcapsule shell. The conformer scaffolds could remain attached to the individual cells as the cells were separated from each other. Therefore, anchorage-dependent mammalian cells were harvested non-disruptively (un-disputed cells) without subjecting them to the typical disruptive detachment procedures used in conventional 2D cultures.

Figure 4:
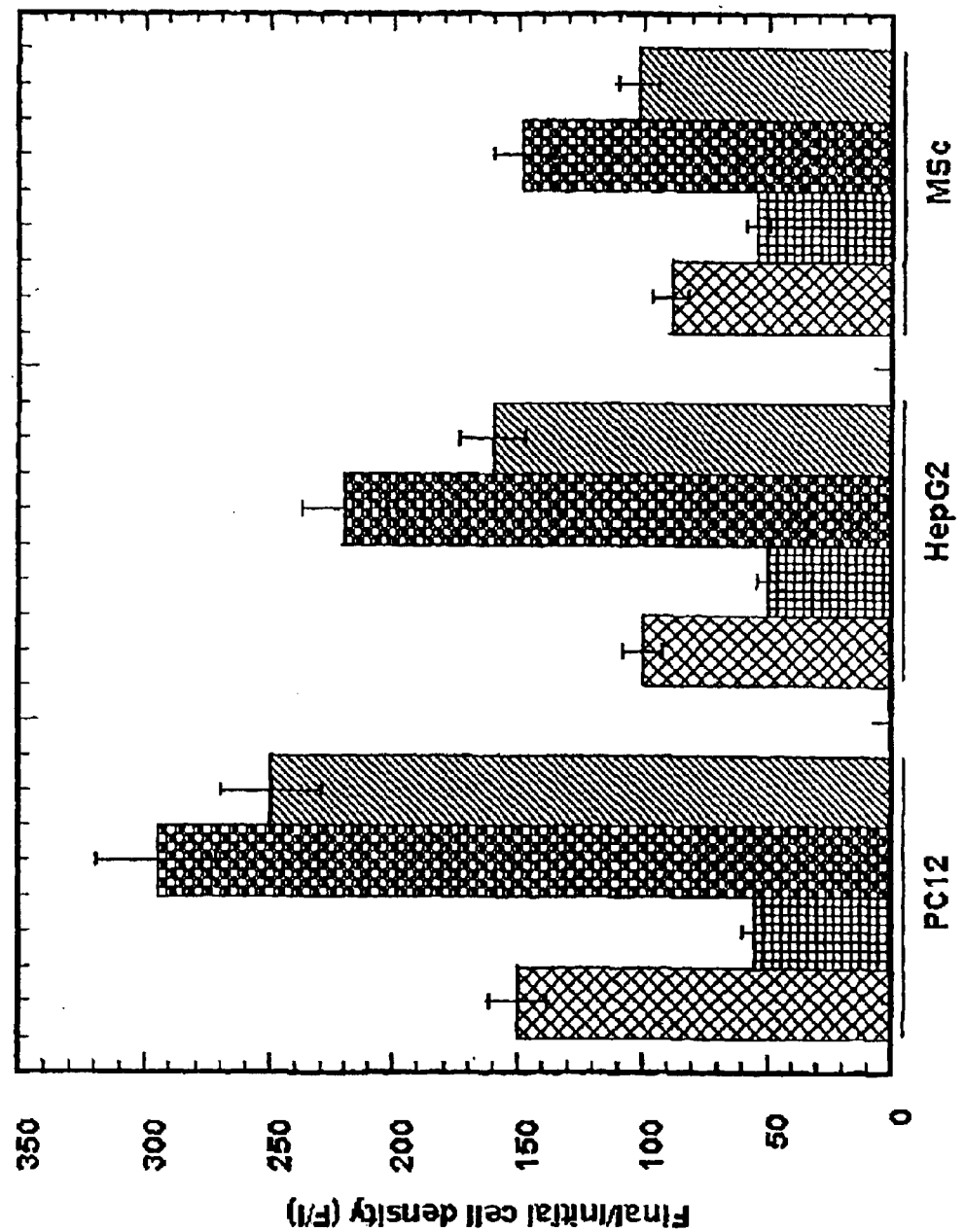
FIG. 4 is a graph illustrating cell re-proliferation of PC 12, HepG2 and MSc cells in the microcapsules.

The harvested cells were encapsulated in the microcapsules at $1 \times 10^6$ cells/ml in 1.5 mg/ml of the modified collagen and allowed to proliferate for 7 days. The PC 12, HepG2, and MSc cells were amplified 150±12, 100±8, and 89±6 times, respectively, in the microcapsules with slightly modified collagen and 295±24, 220±19, and 150±12 times, respectively, with highly modified collagen (FIG. 4). Cell amplification was quantified by calculating the ratio of the final cell density to the initial cell density (FAD. In FIG. 4, ⊞ and ⊠ represent the F/I values for cells cultured in microcapsules with the slightly modified collagen in the completely dissociated and incompletely dissociated state respectively; ⊠ and ⊠ represent the F/I values for cells cultured in microcapsules with highly modified collagen in the completely dissociated and incompletely dissociated state respectively. Harvested cells in single cell state re-proliferated to the full potential while the cell aggregates exhibited a reduced level of re-proliferation It was conceivable that the aggregation observed in the incompletely dissociated cells could inhibit cell proliferation. It was found that the completely dissociated cells could re-proliferate to the full potential (as in FIG. 1) while the incompletely dissociated cells exhibited a reduced level of re-proliferation (FIG. 4). The highly modified collagen could enhance the cell amplification with no significant differences in cell amplification in completely or incompletely dissociated states (FIG. 4).

Un-disrupted cells also exhibit better attachment kinetics, cell morphology and functions than the conventionally cultured cells that were harvested with disruptive detachment procedures. For tissue engineering applications, it is highly desirable to transplant harvested cells that mimic the characteristics in vivo.

The characteristics of PC 12 cells and rat hepatocytes cultured on specific ligand-conjugated polymeric surfaces were examined. Rat hepatocytes were used in place of HepG2 because rat hepatocytes have well-characterized attachment characteristics to specific ligands. Rat hepatocytes also have a well-established functional assay for the cytochrome P450-dependent mono-oxygenase activity, which is a good indicator of the detoxifying ability of the cells.

PC 12 cells interact with the YIGSR peptide-binding domain of laminin. Rat hepatocytes specifically bind to motifs on certain sugar, such as lactose and galactose. The lactose and YIGSR fragment of the laminin were chemically conjugated onto polyester (PET) membranes and the kinetics of the cell attachment to these membranes was measured. It was found that the un-disrupted cells exhibited better attachment kinetics than the conventionally cultured cells (FIG. 5A–B) on binding to these ligand-modified polymer surfaces.

Figure 5A:
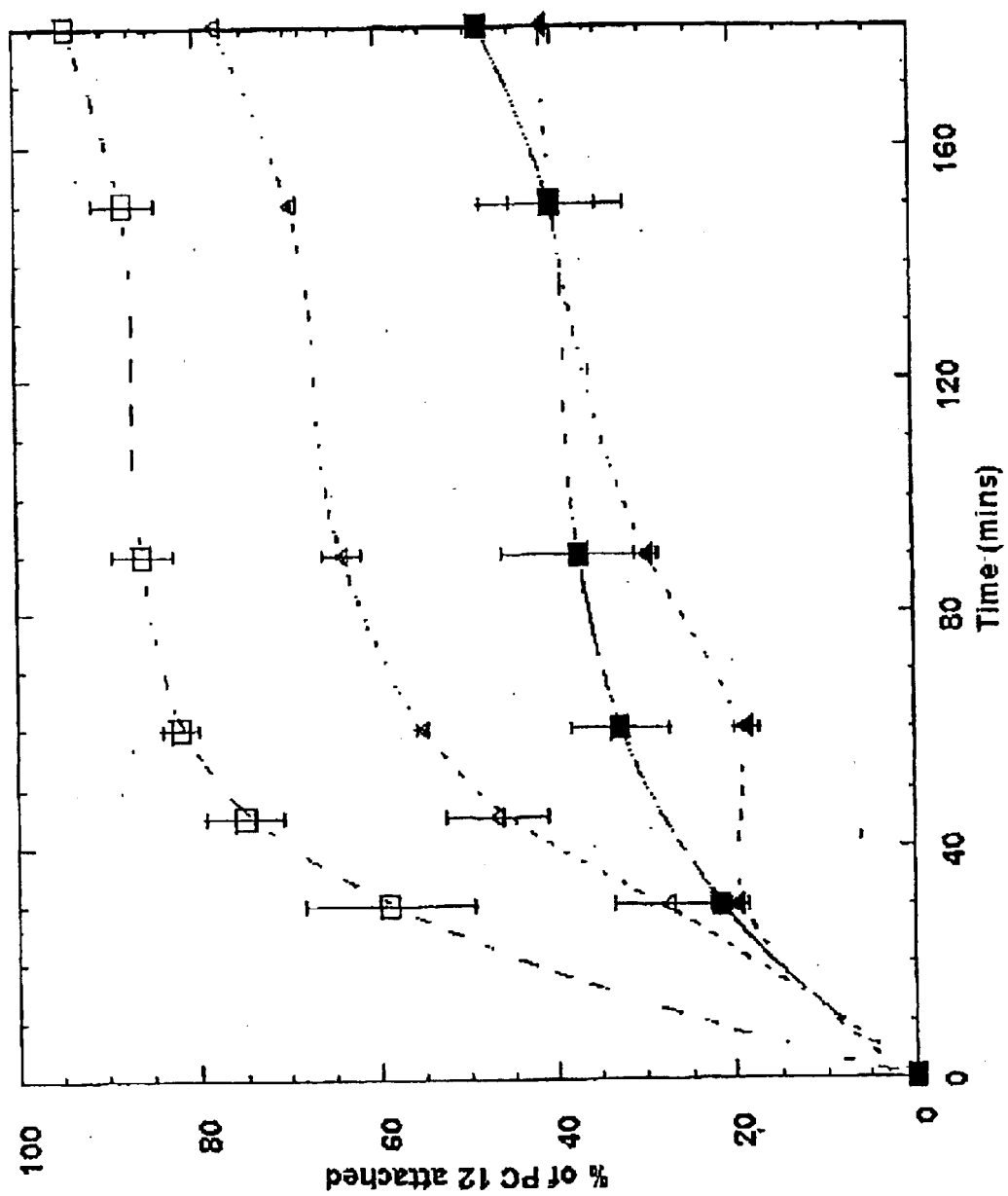
FIGS. 5A–5F illustrate comparison of ligand-specific attachment, cell morphology, and functions of the un-disrupted cells, and conventionally cultured cells.
Figure 5B:
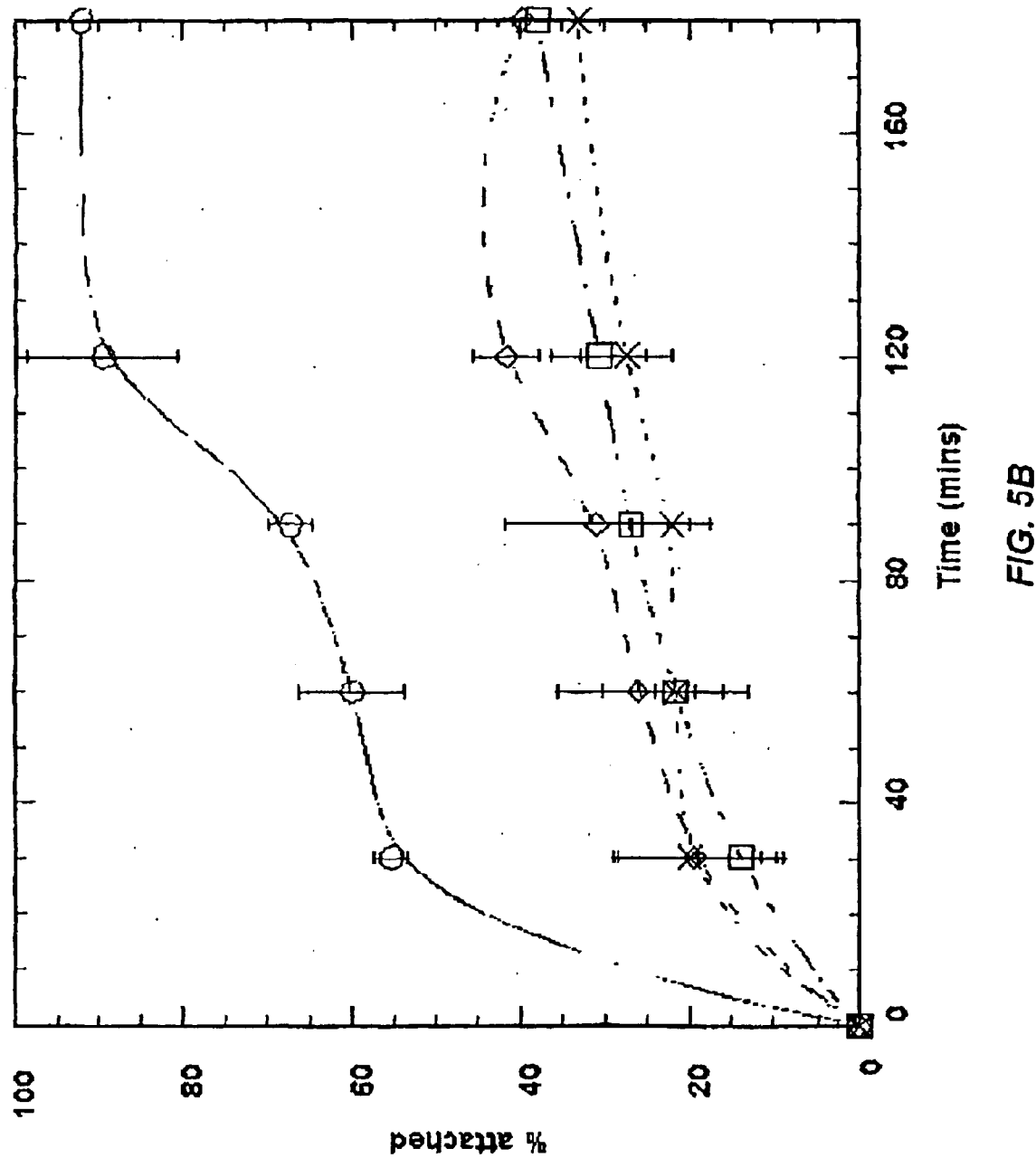

In FIG. 5A, (□) and (■) represent the attachment of the un-disrupted PC 12 cells onto YIGSR-conjugated and plain polyester membranes, respectively, (Δ) and (▲) represent the attachment of the conventionally cultured PC 12 cells onto YIGSR-conjugated and plain polyester membranes, respectively. In FIG. 5B, (○) and (□) represent the attachment of un-disrupted rat hepatocytes onto lactose-conjugated PET cover slip, respectively; (◇) and (x) represent the attachment of the conventionally cultured rat hepatocytes onto lactose-conjugated and plain PET cover slip, respectively. The undisrupted PC 12 cells and rat hepatocytes were found to exhibit better attachment to ligand-conjugated PET cover slip than the conventionally cultured cells.

Figure 5C:
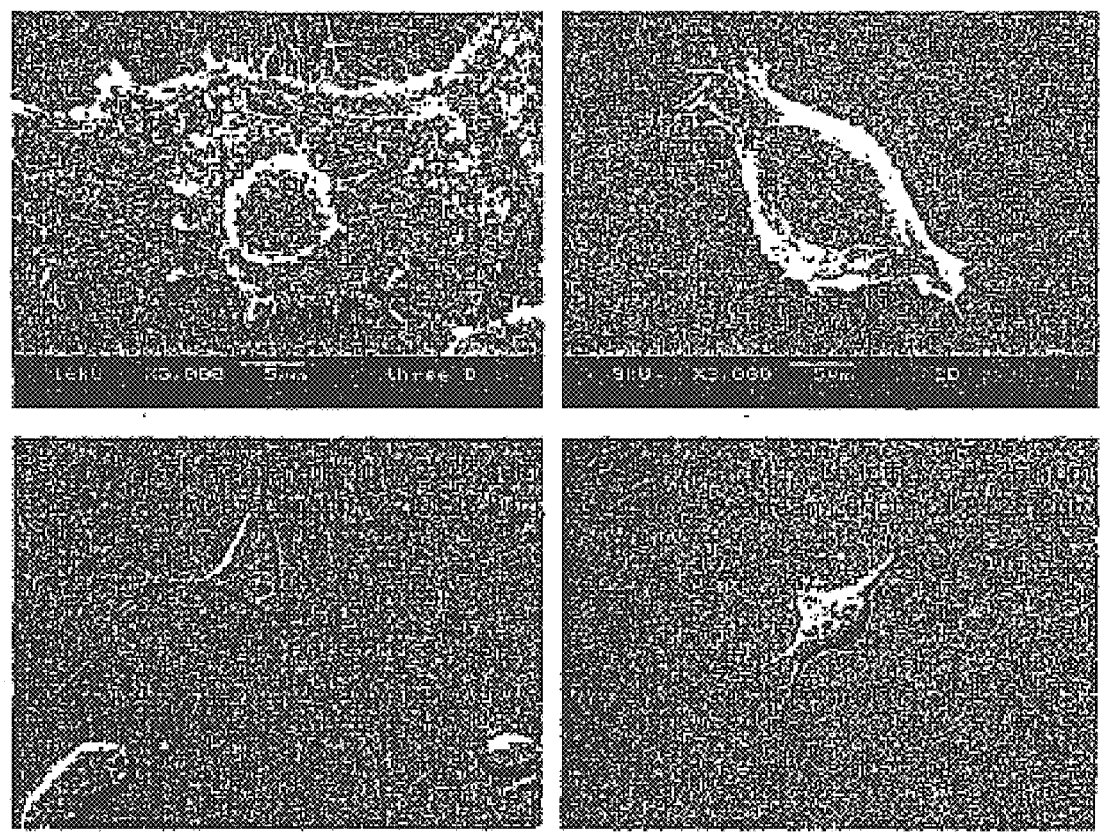

The morphology of PC 12 cells changes in response to extra-cellular microenvironment. The cell morphology of PC 12 cells was examined as they attached to the ligand-conjugated PET membranes. Three hours after the cells were incubated with the membranes, the cells harvested from conventional culture started to attach with spread morphology (FIG. 5C). In contrast, the un-disrupted PC 12 cells exhibited the healthy round morphology by binding to significant amount of extracellular matrices that seemed to have been secreted by the cells (FIG. 5C). Undifferentiated PC 12 cells normally exhibit round morphology until after many passages. Therefore, the un-disrupted cells seem to preserve better cell morphology and matrix-secretion than the conventionally cultured cells.

In FIG. 5C, the top left panel represents the undisrupted PC 12 cells 3 hours after attached to YIGSR-conjugated PET cover slip; the top right panel represents the conventionally cultured PC 12 cells. The un-disrupted PC 12 cells have secreted significant amount of the extracellular matrices than the conventionally cultured cells. The bottom left panel represents the un-disrupted PC 12 cells 48 hours after nerve growth factor induction; the bottom right panel represents conventionally cultured PC 12 cells. The maximum length= $\Sigma$(length of the longest neurite on each cell)/n. The mean length=$\Sigma$(mean length of all the neurites on each cell)/n (n=50 cells). The un-disrupted PC 12 cells show longer neurite extension tan the conventionally cultured cells.

The PC 12 cells can be induced to form neurites by nerve growth factor. The maximum and mean lengths of the neurite extension are good measures of the PC 12 cellular functions. The lengths of the neurites extended from PC 12 cells 48 hours after induction by nerve growth actor were measured. It was found that neurites extended from the undisrupted PC 12 cells were 2-fold longer, in terms of both maximum and mean lengths, than the neurites extended from the conventionally culled PC 12 cells (FIG. 5C).

Figure 5D:
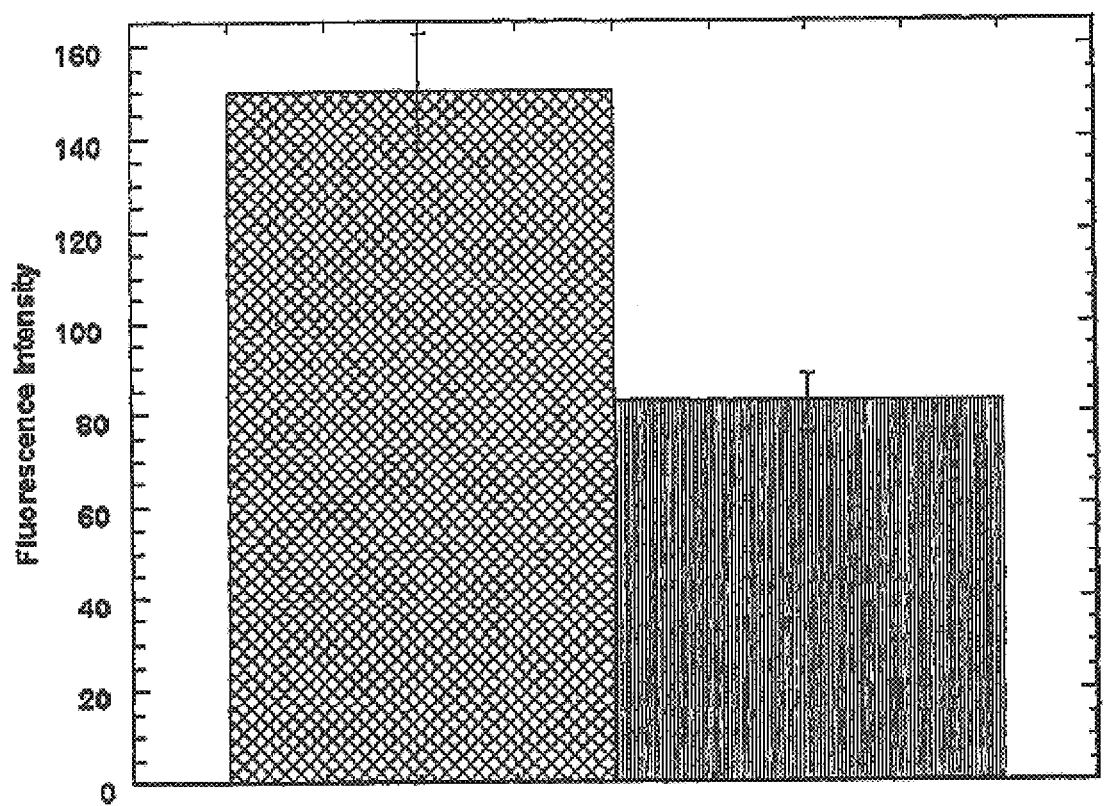

The cytochrome P450-dependent mono-oxygenase activity of the rat hepatocytes also was measured 7-ethoxyresorufin can be converted by the cytochrome P450 dependent mono-oxygenase into a fluorescent product, resorufin. The amount of the fluorescence was imaged and quantified using a confocal microscope. The un-disrupted rat hepatocytes exhibited a 2-fold higher detoxification function than the conventionally cultured cells (FIG. 5D) 3 hours after attaching to lactose-conjugated PET membranes. Therefore, the un-disrupted cells have demonstrated better attachment, morphology, and functions than the conventionally cultured cells. FIG. 5D illustrates detoxification function of the rat hepatocytes (as measured by the cytochrome P450-dependent mono-oxygenase activity assay attached onto the lactose-conjugated PET cover slip). The symbols ⊞ represents the detoxification function of the un-disputed cells; the symbol ▨ represents the conventionally cultured cells. The undisrupted rat hepatocytes exhibit 2-fold higher detoxification function than the conventionally cultured cells 3 hours after attached to the lactose-conjugated PET cover slip (n=150).

Figure 5E:
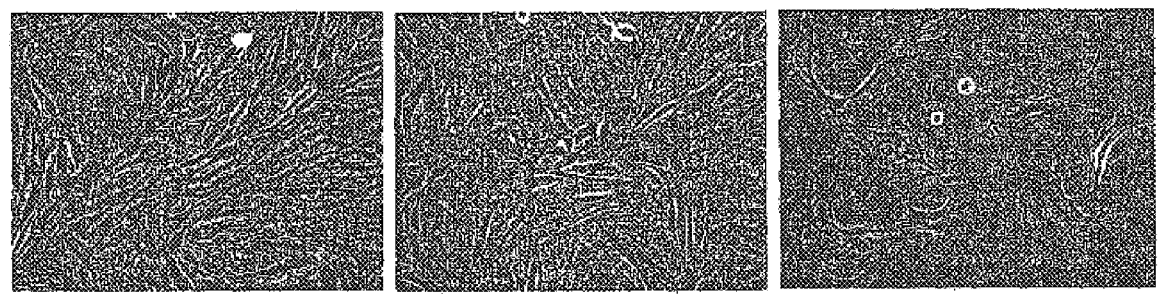

The morphology of the MSC cells on a 2D culture changes with response to the numbers of passages and tend to undergo spontaneous differentiation. The morphology of the undisrupted cells and the conventionally culture 2D cells were observed as they attached onto the tissue culture polystyrene dish after a month of continuous culture. In a suitable environment, the heterogeneous cell populations can differentiate into several lineages depending on the induction factors and environments. One typical characteristic of these cells cultured in 2D is that they have limited proliferative capacity (from about 7–13 passages). Most cells exhibit a slowed proliferation (increasing doubling time) after about 10 passages, and almost completely stop proliferation after about 12 or 13 passages. After that time, the cells randomly differentiate and lift up from the culture dish and float up into culture media (FIG. 5E). The cells typically have a doubling time of about 48 hours, i.e., the cells can proliferate for about $2^{12}$ (=4096) folds per isolation from bone marrow hen cultured in 2D.

Figure 5F:
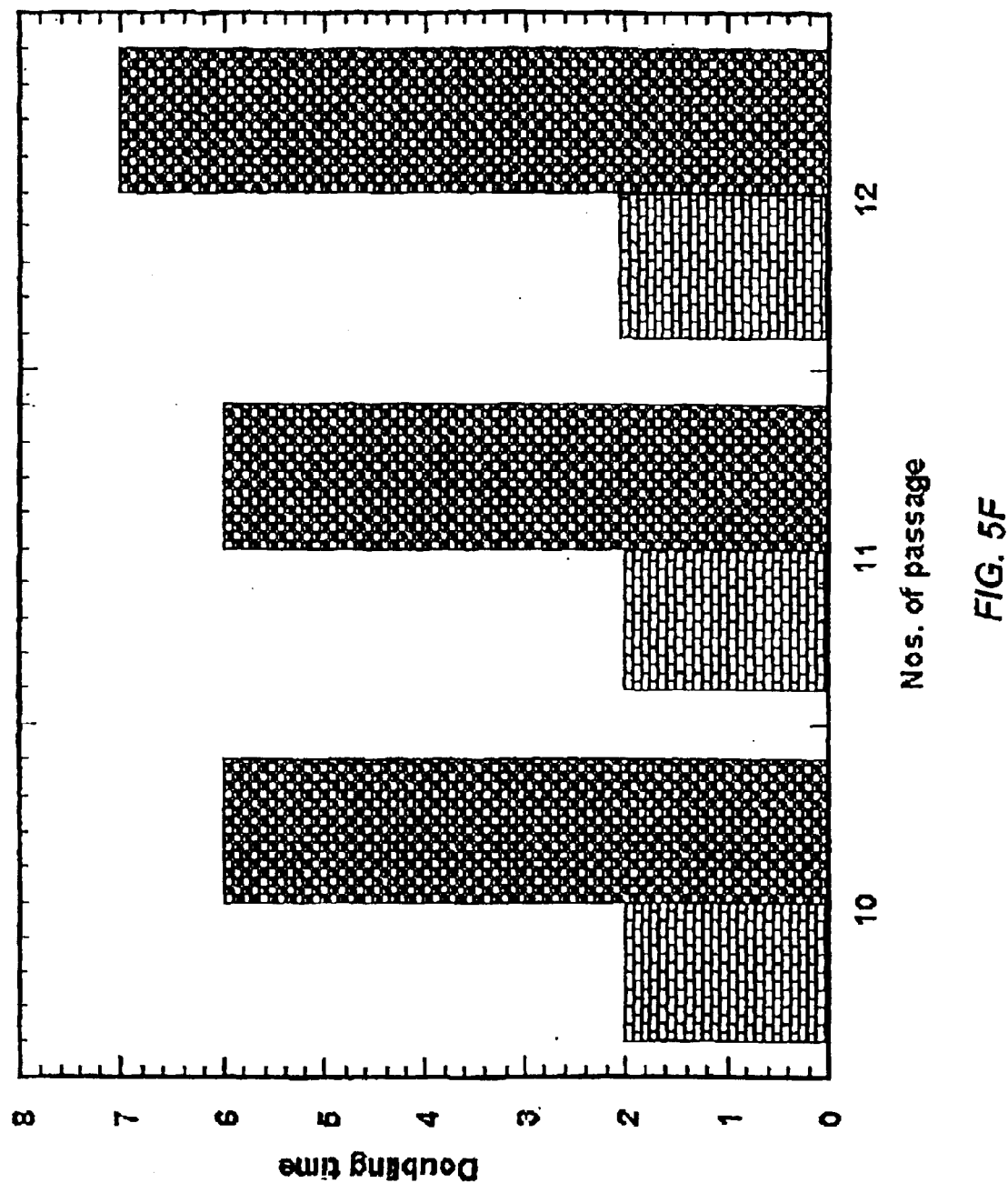

In FIG. 5E, the left panel represents the 2D cells at passage 5, 48 hours upon attachment tissue culture polystyrene dish. The middle panel represents the un-disrupted cells at passage 11, 48 hours upon attachment onto tissue culture polystyrene dish. The night panel represents the 2D cells at passage 14, which have shown a de se in rate of proliferation. The un-disrupted cells and the 2D cells assume the well-spread morphology at confluency. FIG. 5F illustrates the doubling time of the cells. The symbol ▦ represents the doubling time of the un-disrupted cells. The symbol ▤ represents the doubling time of the conventionally cultured cells.

When the cells were cultured in the 3D system of the present invention, about a 100- to 160-fold amplification was observed in 57 days. Thus, the doubling time was reduced to about 24 hours in the microcapsules. These cells were cultured in microcapsules for 35 days, which is equivalent to a $2^{35}$ (~$3.4 \times 10^{10}$) fold amplification. In terms of the age of the cells, such amplification is equivalent to about 35 passages in 2D culture. At the time of filing of this application, the cells were still proliferating in microcapsules as readily (e.g., with the same steady rate) as when they were first isolated from the bone marrow. When these cells were plated onto a 2D culture plate, they exhibited the same morphology, and the same doubling time (48 hours) in 2D culture as those cells freshly isolated (in contrast to the cells cultured in 2D culture for 12 passages, which then stopped proliferation).

The three-dimensional cell culture system of the present invention can greatly extend the proliferative capacity of many primary cells isolated from tissues, especially those precursors and various stem cells from bone marrow and other possible sources such as cord blood, adult blood, fat, etc., for truly large-scale production of such cells. This in urn will greatly facilitate or made possible the various applications (e.g., Plantation, tissue engineering, etc.) using autologous or allogenic cell sources. If sufficient adult stem cells can be amplified for various applications, this potentially overcomes one of the primary limitations of adult stem (AS) cells, which in turn could avoid the ethically complicated use of embryonic stem (ES) cells altogether.

Tissue engineering applications can greatly benefit from the un-disrupted cells obtained by the 3D culture of the present invention. Numerous efforts have been undertaken to develop and improve cell attachment. It is believed that the un-disrupted cells exhibiting the improved attachment kinetics can complement these efforts. The requirements for cells to recover from the typical detachment damages experienced by the conventionally cultured cells are avoided so that the un-disrupted cells can interact with the engineered biomaterials surfaces immediately after harvesting. Multiple types of cells can be seeded sequentially within a short period of time to better control the formation of complex issue constructs. These un-disrupted cells also have intact cell surface receptors and other membrane components that can enhance the interaction between these undisrupted cells and other cells or extra-cellular matrices to generate functioning tissues when transplanted in vivo for tissue repair and regeneration.

Furthermore, the microencapsulated cells can be cultured in well-established macro-environments such as the packed-bed and fluidized-bed bioreactors for large-scale production of highly functional anchorage-dependent cells for various applications.

EXAMPLE

The following example is illustrative of preferred aspects of the invention and should not be construed to limit the claims in any way. The example illustrates preparing a three-dimensional cell culture with hepatocyte, PC12, and MSc cells. All reagents were purchased from Sigma-Aldrich unless otherwise indicated Ter-Polymer Preparation Ter-polymer of methacrylic acid (MAA), 2-hydroxyethyl metacrylate (HEMA), and methyl methacrylate (MMA) was synthesized by solution polymerization in 2-propanol using 2,2'-azobisisobutyronitrile (AIBN) as initiator. The monomers were distilled under nitrogen at reduced pressure. The polymerization was performed with an initiator concentration of 0.1 mol % of monomers under nitrogen with a magnetic stirrer at 78° C. in an oil bath. The molar feed ratio of MAA, HEMA, and MMA was fixed at 25:25:50 or other ratios as desire and the ratio of total monomer to solvent at 1:6 (W/V). The reaction was allowed to proceed for overnight and quenched by cooling to room temperature. The polymer was precipitated by addition to a large excess of petroleum ether. The precipitate was re-dissolved in a minimum volume of ethanol, and re-precipitated in distilled water. Recovered polymer then was dissolved in a 1 M sodium hydroxide solution, and further purified by repeated dialysis against distilled water with MWCO of 3500, and lyophilized. The yield of the polymer was found to be 63%. The polymer composition was determined by proton NMR and the molar ratio of MAA, AMA, and MMA was found to be 20.4:27.4:52.2 for the molar feed ratio of 25:25:50. The molecular weight of the ter-polymer before dialysis was determined by GPC (with THF as eluent) to be 30,000.

Modification of Collagen at 4° C.

Collagen cam be modified to be cationic and anionic by the removal of either the negative or the positive charge from the collagen chains. In this case, cationic collagen was obtained through the modification of the carboxyl group by esterification with low molecular weight alcohol. 20 ml of stock solution (3 mg/ml) of collagen (Vitrogen 100, Collagen Corp., Palo Alto, Calif.) was fist precipitated with 400 ml of acetone. The precipitated collagen was dissolved in 200 ml of 0.1 M HCl containing methanol (Merck), stirred at 4° C. for 6 days under sterile conditions. The lyophilized modified collagen can then be stored up to 6 months in −20° C. in the presence of desiccant. The modification was monitored by titration. Titration of the natural collagen gave a typical titration curve of a mixed acid or a dibasic acid, while that of modified collagen gave a typical titration curve of a week monobasic acid, indicating that most carboxyl groups have been esterified in modified collagen. In addition, neutralization of the modified collagen needs less sodium hydroxide than that of the natural collagen, indicating that the polymer chain of the modified collagen has less ionic groups because of the esterification of the carboxyl groups.

Modification of Collagen at Room Temperature

Collagen can be modified to be cationic and anionic by the removal of either the negative or the positive charge from the collagen chains. In this case, cationic collagen was obtained through the modification of the carboxyl group by esterification with low molecular weight alcohol (e.g. methanol). 20 ml of stock solution (3 mg/ml) collagen (Vitrogen 1000, Collagen Corps Palo Alto, Calif.) was first precipitated with 400 ml of acetone. The precipitated collagen was dissolved in 200 ml of 0.1 M HCl containing methanol (Merck), stirred at room temperature for various amount of time (3, 6, 24 & 48 hours) under sterile conditions. The modified collagen solution was dialyzed for 2 days until the pH reached 5 and lyophilized. The lyophilized modified collagen can then be stored up to 6 months in −20° C. in the presence of desiccant. The degree of modification was monitored by titration. Titration of the natural collagen gave a typical curve of a mixed acid or a dibasic acid, while that of modified collagen gave a typical titration curve of a weak monobasic acid, indicating that most carboxyl groups have been esterified in modified collagen. In addition, neutralization of the modified collagen needs less sodium hydroxide than that of the natural collagen, indicating that the polymer chain of the modified collagen has less carboxylic protons because of the esterification of these carboxyl groups. The collagen modified at room temperature has a higher degree of freedom in terms of the amount of positive charges than those modified at 4° C. as described previously. This allows a wider range of collagen concentrations to be used to form microcapsules since the previous microcapsules are limited by the charges on modified collagen.

Isolation of Hepatocytes

Hepatocytes were harvested from male, Wistar rat, weighing from 250–300 g by a 2-step in situ collagenase perfusion as described previously with some modifications. The rat was given 100 U/kg of heparin 30 minutes before anesthesia. Pentobarbital was administered at a dose of 30 mg/kg, intra-peritoneally at the start of the operation. After laparotomy, a portal cannula was placed and fixed in a position along the portal vein. A cut was rapidly made in the lower vena cava. In the first 2–3 minutes, pre-perfusion (with $Ca^{2+}$-free perfusion buffer) was performed while the liver remained in situ. The perfusate flow was started at a rate of 50 ml per minute. While pre-perfusion was carried out, the liver was transferred to a petri-dish and pled in a position similar to its in situ site. After 10 minutes of pre-perfusion with $Ca^{2+}$-free medium, the liver was then perfused with recirculating 0.05% collagenase buffer for another 10 minutes. This was terminated when the vena cava ruptured. The entire perfusion procedure was performed under oxygenation that greatly improved the cell viability. The cells were liberated from the connective vascular tissue and re-suspended in fresh growth medium. This was followed by incubation of the cell suspension in a 37° C. $CO_2$ incubator for 30 minutes. The cell suspension was then filtered through a nylon mesh with a 60 $\mu$m pore size to ter remove the connective tissue debris. The filtrate was then centrifuged at 50 g for 1 minute to obtain the cell pellet. The cells were collected and washed twice with growth medium. The viability of the hepatocytes was determined to be 90–95% in all cases using the conventional Trypan Blue exclusion test.

Preparation of Microencapsulated PC12 Cells

Microencapsulation was performed at room temperature with the aid of a syringe pump (IVAC P6000, Alaris Medical Systems, San Diego, Calif.). The PC-12 cells were suspended in a modified collagen solution that was prepared by first dissolving the lyophilized modified collagen in Phosphate Buffered Saline (PBS) to obtain a collagen concentrations of 0.5, 1.0, and 1.5 mg/ml. The cell suspension was maintained at 4° C. before the experiment to prevent the gelation of the collagen solution. The PC-12 cells summon was extruded from a 30.5-gauge needle attached to the syringe pump at various flow rates suitable into a 10%–17% ter-polymer solution unless otherwise stated. Thus, the positively charged collagen molecules bound to the negatively charged ter-polymer molecules at the outer surface of the microcapsules to form a polyelectrolyte complex. The microcapsules were incubated at 37° C. for an hour to allow the collagen to gel before the microcapsules were harvested by sedimentation method and washed twice with 1×PBS for further culturing.

Modifying the charges of the positively charged collagen and the concentration of the negatively charged ter-polymer controls the thickness of the ter-polymer shell A 0.5 mg/ml collagen has less positive charges thin a 1.5 mg/ml collagen. The thickness of the ter-polymer shell in the range of 2–5 An was found to provide optimal mass transport properties. Therefore, 10% of the ter-polymer is needed to complex coacervate 0.5 mg/ml collagen but 17% ter-polymer is needed to complex coacervate 1.5 mg/ml collagen to form 2–5 µm shell. If a 10% ter-polymer is used for 1.5 mg/ml collagen with high charge density (modified at room temperature for one day), then a much thicker shell is formed which imps the mass transport properties and leads to central necrosis at center of the microcapsules.

Preparation of Microencapsulated Hepatocytes

Microencapsulation was performed at room temperature with the aid of a syringe pump. Briefly, the hepatocytes were suspended in a modified collagen solution that was prepared by first dissolving the lyophilized modified collagen in Phosphate Buffered Saline (PBS) to obtain a collagen concentration of 1.5 mg/ml. The hepatocyte suspension was maintained at 4° C. before the experiment to prevent the gelation of the collagen solution. The hepatocyte suspension was extruded from an 18½ gauge needle attached to a syringe pump at various flow rates into 10% ter-polymer solution. Thus, the positively charged collagen molecules bound to the negatively charged ter-polymer molecules at the outer sure of the microcapsules to form a polyelectrolyte complex. The microcapsules were incubated at 37° C. for one hour to allow the collagen to gel before the microcapsules were harvested by sedimentation method and washed twice with 1×PBS for further culturing.

Cell Culture

The microencapsulated cells were cultured for the required amount of time in 35 mm polystyrene dishes in a humidified atmosphere at 370° C. with 5% $CO_2$ Culture media [PC12: DMEM supplemented with 5% horse serum (GIBCO Laboratories, Chagrin Falls, Ohio) and 10% fetal bovine serum (GIBCO Laboratories, Chagrin Falls, Ohio); HepG2: DMEM supplemented with 10% fetal bovine serum; rabbit mesenchymal stem cells: DMEM supplemented with 15% fetal bovine serum and 1500 mg/L of glucose and rat hepatocytes: Hepatozym-SFM (GIBCO Laboratories, Chagrin Falls, Ohio)] were replaced every two days. Conventional culture of the cells in 2D were performed as described in (1) Jauregui, "Cell Adhesion to Biomaterials: The Role of Several Extracellular Matrix Components in the Attachment of Non-transformed Fibroblasts and Parenchymal Cells," ASAIO Trans 33, 6674 (1987); (2) Gutsche, A. T. et al., "Rat Hepatocyte Morphology and Function on Lactose-Derivatized Polystyrene Surfaces," Biotechnology and Bioengineering 49, 259–265 (1996); and (3) Hu, M. Y. et al., "Effects of Hepatocytes Growth Factor on Viability and Biotransformation Functions of Hepatocytes in Gel Entrapment and Monolayer Culture," Crit Care Med 23, 1237–1242(1995).

PC12 and HepG2 cells were purchased from ATCC. Rat hepatocytes were isolated as describe in China, S. M. et al., "Hepatocyte Encapsulation for Enhanced Cellular Functions," Tissue Eng 5, 481–496 (2000). Mesenchymal stem (MSC) cells enriched low density bone marrow mononuclear cells (BMMNC) were isolated as follows: Bone marrow was aspirated from iliac crest of NZW rabbits and collected into 50 ml polypropylene tubes with 1000 units/mil preservative-free heparin and thoroughly mixed. Low density BMMNCs were by density gradient centrifugation over Ficoll (1.077 g/ml) at 400×g for 30 minutes. The BMMNC layers were removed by pipet and rinsed in PBS, and cultured in suitable media as described above.

Cell Splitting and Harvesting

The un-disputed cells were harvested from the microcapsules by passing the microcapsules through a 1 mm diameter plastic nozzle at a flow rate of 8 ml/min. The cells released from the microcapsules were centrifuged at 80×g for 1 minute to remove the large pieces of the broken microencapsule shell. The supernatant containing the cells released from the broken microcapsules were collected and centrifuged for an additional 3 minutes at 800×g to remove the liquid collagen. The cell pellets were rinsed with buffer, Le., re-suspended in phosphate buffered saline (PBS) and re-centrifuged again. The cell pellets were then re-suspended in fresh culture media for re-proliferation or use immediately for applications. The number of cells amplified was determined by counting the cells released from the microcapsules with the aid of a hemocytometer.

Light Microscope Imaging of the Microcapsules

Live cells were imaged with a confocal microscope (Olympus FLUOVIEW 300, Tokyo). To visualize the formation of the "conformer scaffolds", the modified collagen was labeled with FTTC by dissolving mg of FTTC in 10 mL of 1.5 mg/mL modified collagen solution overnight, followed by extensive dialysis for 24 hours to remove the unlabelled FTTC molecules. The lyophilized labeled collagen can be stored in −20° C. in darkness for up to 6 months. The microcapsules were processed for scanning electron microscopy and imaged with a JOEL 5600 LV SEM.

Peptide Conjugation to PET Membranes

Thermanox cover slips (PET cover slip, NUNC, Naperville, Ill., USA) were cleaned by rinsing with solvents (in a sequence of Water-Methanol-Hexane-Methanol-Water). Clean cover slips were placed into 24-well culture plates containing 1 M NaOH (1 ml) in each well and hydrolyzed for 4 hour at room temperature with shaking. The cover slips were then rinsed several times with 1 M HCl and distilled water. The resulting cover slips were treated in a mixed solution, which cons 0.1 M MES, 1 mg/ml NHS, 10 mg/ml EDC and 0.5 mg/ml YIGSR peptide for more than 4 hours on a platform shaker. Finally, the cover slips were rinsed with PBS once and with 4 N NaCl 3 tines, then with PBS for several times before use.

Lactose Conjugation to PET Membranes

Thermanox cover slips were first aminated by incubating with 50% aqueous ethylene diamine solution for 8 hours at 40° C., and rinsed with excess amount of tetrahydrofuran and de-ionized water. The aminated PET cover slips were then incubated in 0.1M sodium borate buffer (pH 9.3) containing 10 mg/ml lactose and 10 mg/ml sodium cyanoborohydride at 40° C. for 48 hours followed by extensive rinsing with 4 N NaCl and de-ionized water. The amount of the lactose/galactose conjugated to the PET membranes was determined by counting the 14C-labelled lactose (ICN Biomedicals, Inc., Aurora, Ohio) in the reaction. Cells attached to the membranes were quantified by counting the percentage of unattached cells among the total number of cells incubated with the membranes.

Morphological Assay

Mesenchymal stem cells harvested from the microcapsules or the 2D culture were seeded onto 35 mm tissue culture dishes and incubated for 48 hours in 37° C. with 5% $CO_2$. The morphology of the cells was imaged with an inverted microscope with Hoffman optics.

Functional Assays

PC 12 cells harvested from the microcapsules or 2D culture were seeded onto collagen-coated membranes and induced with 20 ng/ml of nerve growth factor (Baldwin, S. P. et al., "PC12 Cell Aggregation and Neurite Growth in Gels of Collagen, Laminin and Fibronectin," *Int J Dev Neurosci* 14, 351–364 (1996)) for 48 hours. The cells were fixed with 3.7% Formalin for 10 minutes, imaged and the maximum and the mean neurite lengths quantified with a confocal microscope. The cytochrome P450-dependent mono-oxygenase activity of rat hepatocytes was measures Data from three independent experiments were analyzed and values are represented as mean±standard error of means.

It will be apparent to those skilled in the art that various modifications and variations can be made in the compositions and methods of the present invention without departing from the spirit or scope of the invention thus, it is intended that the present invention cover the modifications and variations of this invention provided they come within the scope of the appended claims and their equivalents

What is claimed is:

1. A non-disruptive three-dimensional system for culturing one or more anchorage-dependent cell types, the system comprising a plurality of hollow microcapsules each containing an inner extracellular matrix in contact with at least one cell and an outer shell of synthetic polymer surrounding the extracellular matrix;

wherein cells in contact with the extracellular matrix are cultured in three dimensions inside of the hollow microcapsules;

wherein said microcapsules are permeable to nutrients necessary to sustain normal metabolic functions of the cells and to toxins released by the cells; and wherein said outer shell has a thickness of from about 1 to about 40 µm and is rupturable with mechanical agitation to harvest the cultured cells.

2. The cell culture system of claim 1 wherein the ratio of the number of cells at the end of a culture period to the number of initially seeded cells is at least 10:1.

3. The cell culture system of claim 1 wherein said extracellular matrix is selected from the group consisting of cationic collagen, anionic collagen, anionic esterified hyaluronic acid, anionic amine-modified hyaluronic acid, fibronectin, and laminin.

4. The cell culture system of claim 3 wherein said extracellular matrix comprises a cationic collagen at a concentration of from about 0.2 to about 3.5 mg/ml.

5. The cell culture system of claim 1 wherein said synthetic polymer comprises an acrylate ter-polymer of methacrylic acid, hydroxyethyl methacrylate, and methyl methacrylate.

6. The cell culture system of claim 1 wherein said anchorage-dependent cells comprise one or more cell types selected from the group consisting of pheochromocytoma cells, hepatocyte cells, and mesenchymal stem cells.

7. The cell culture system of claim 1 wherein said anchorage-dependent cells comprise at least two cell types.

8. The cell culture system of claim 7 wherein said anchorage-dependent cells comprise at least three cell types.

9. A method of culturing anchorage-dependent cells in a three-dimensional cell culture system comprising:

encapsulating anchorage-dependent cells in a hollow microcapsule comprising an inner extracellular matrix surrounding at least one cell and an outer shell of synthetic polymer surrounding and supporting the matrix; wherein cells in contact with the extracellular matrix are cultured in three dimensions inside of the hollow microcapsule; wherein said microcapsule is permeable to nutrients necessary to sustain normal metabolic functions of the cells and to toxins released by the cells; and wherein said outer shell has a thickness of from about 1 to about 40 µm;

applying agitation to the microcapsule after a predetermined time to rupture the outer shell; and removing the extracellular matrix to recover the cells.

10. The method of claim 9 wherein the ratio of the number of cells at the end of a culture period to the number of initially seeded cells is at least 10:1.

11. The method of claim 9 wherein said extracellular matrix is selected from the group consisting of cationic collagen, anionic collagen, anionic esterified hyaluronic acid, anionic amine-modified hyaluronic acid, fibronectin, and laminin.

12. The method of claim 9 wherein said extracellular matrix comprises a cationic collagen at a concentration of from about 0.2 to about 3.5 mg/ml.

13. The method of claim 9 wherein said synthetic polymer comprises an acrylate ter-polymer of methacrylic acid, hydroxyethyl methacrylate, and methyl methacrylate.

14. The method of claim 9 wherein said anchorage-dependent cells comprise one or more cell types selected from the group consisting of pheochromocytoma cells, hepatocyte cells, and mesenchymal stem cells.

15. The method of claim 9 wherein said anchorage-dependent cells comprise at least two cell types.

16. The method of claim 9 wherein said anchorage-dependent cells comprise at least three cell types.

* * * * *